United States Patent [19]

Plotkin

[11] Patent Number: 5,106,995

[45] Date of Patent: Apr. 21, 1992

[54] PRODUCTION OF LACTONES FROM DIOLS

[75] Inventor: Jeffrey S. Plotkin, Monsey, N.Y.

[73] Assignee: ISP Investments Inc., Wilmington, Del.

[21] Appl. No.: 347,647

[22] Filed: May 5, 1989

[51] Int. Cl.$^5$ ............................................ C07D 307/32
[52] U.S. Cl. .................................. 549/273; 549/273; 549/295; 549/299; 549/323
[58] Field of Search ............... 549/295, 273, 274, 323, 549/299

[56] References Cited

U.S. PATENT DOCUMENTS 4,465,847  8/1984  Shvo .................................. 549/295

OTHER PUBLICATIONS

H. Mercker, et al., Ulmanns *Encyclopedia of the Chemical Industry,* "Batgrolactone," A4, pp. 495–498 (1957).
S. Murahashi, et al., *J. Org. Chem.,* "Ruthenium-Catalyzed Oxidations of Alcohols and Aldehyde . . .," 52, (19), 4319–4327 (1987).
S. Torii, et al., *J. Org. Chem.,* "Indirect Electrooxidation of Alcohols and Aldehydes by Using . . .," 51 (2), 155–161, (1986).
R. A. Sheldon, et al., "Metal-Catalyzed Oxidations of Organic Compounds," Chapter 12, pp. 350–356, Academic Press, New York (1981).
J. March, "Advanced Organic Chemistry," 2nd ed., p. 363, McGraw-Hill Book Co., New York (1977).

*Primary Examiner*—Richard L. Raymond
*Assistant Examiner*—Mark W. Russell
*Attorney, Agent, or Firm*—McAulay Fisher Nissen Goldberg & Kiel

[57] ABSTRACT

A method for converting 1,4 and 1,5 aliphatic saturated diols to lactones is disclosed wherein the diol is reacted with a chemical oxidizing agent and a ruthenium containing catalyst at temperatures substantially less than 200° C. The reaction proceeds quickly and produces high yields of the desired product.

7 Claims, No Drawings

PRODUCTION OF LACTONES FROM DIOLS

BACKGROUND OF THE INVENTION

1. Field of the Invention

This invention pertains to the field of conversion of diols to lactones by oxidation in the presence of a catalyst. More particularly, it relates to the improved production of lactones at low temperatures utilizing ruthenium containing catalysts.

II. Description of the Prior Art

It is known to convert diols to lactones by heating the diol in the presence of a copper chromite catalyst. See, for example, Ulmanns Encyclopedia of the Chemical Industry, Vol. A4, p. 495–498. The general reaction sequence using a butane-1,4-diol as starting material, is as follows:

Reaction Sequence 1

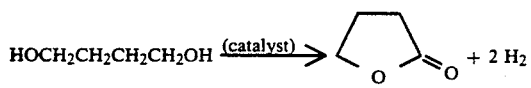

The major problem, however, with this reaction is that it requires excessively high temperatures, namely, temperatures in excess of 200° C. Consequently, if one is preparing a lactone which is thermally sensitive, the high temperature of preparation severely inhibits or renders impossible the carrying out of the dehydrogenation reaction since any product which is formed is destroyed.

It has also been reported that soluble, homogeneous ruthenium complexes can promote dehydrogenation of 1,4-diols if appropriate hydrogen acceptors are present. S. Murahashi, et al., J. Org. Chem., 1987, 52, 4319.

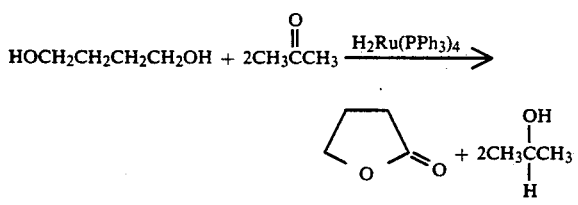

These reactions also require elevated temperatures, e.g., 120–200° C., in order to process at reasonable rates. Also, the catalysts are quite expensive.

It is also known that ruthenium tetroxide is capable of acting as a stoichiometric oxidant for converting alcohols to ketones, aldehydes to acids and ethers to esters or lactones. It is further known that ruthenium can be used in catalytic amounts in the form of ruthenium trichloride or ruthenium oxide if used with an oxidant, such as, sodium hypochlorite to convert ethers to esters. (See "Metal-Catalyzed Oxidations of Organic Compounds" by R.A. Sheldon and J.K. Kochi, Academic Press (1981), Chapter 12.) Indirect electrooxidation of alcohols and diols to acids and lactones, respectively, has been reported using ruthenium-based catalyst system. This was accomplished by utilizing a double mediating system of $RuO_4/RuO_2$ and $Cl^+/Cl^-$ redoxes in an aqueous-organic two-phase system. See J. Org. Chem., 1986, 51, p. 155–161.

SUMMARY OF THE INVENTION

I have discovered a method for producing lactones from 1,4 and 1,5 saturated aliphatic diols which can be conducted at temperatures substantially less than 200° C. and which proceeds with relative rapidity and produces high yields of the desired product. More particularly, I have discovered that this can be accomplished by reacting the starting diol in the presence of a chemical oxidizing agent and a ruthenium containing catalyst. The reaction is carried out at a temperature below 100° C. The preferable temperature range for the reaction is from about −20 to 50° C. Preferably, the reaction is carried out at ambient temperatures. Thereafter, the lactone is recovered from the reaction mixture.

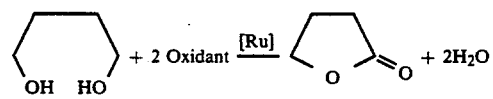

DESCRIPTION OF THE PREFERRED EMBODIMENT

A variety of saturated aliphatic 1,4 and 1,5 diols can be utilized with the present invention. The diols may be substituted with functional groups which are resistant to oxidation, for example, esters, halogen, and cyano groups. Some examples are given in the table. As shown in the Table, 1,4-butane diol and 1,5-pentane diol were oxidized smoothly with high selectivity to the butyrolactone and valeralactone, respectively. 2-Methyl-1,4-butanediol was oxidized to two isomers, namely, 3-methyl butyrolactone and 4-methyl-butyrolactone. Dimethylolnorbornane was also cleanly oxidized in high yield to its corresponding lactone. Diethylene glycol cyclized much more slowly to dioxanone; other unidentified compounds were also found as shown by gas chromatography.

Certain functional groups do not respond desirably to the conditions required in the inventive process. Two examples are butanetriol and 1,4-butenediol. In the case of butanetriol, nearly five equivalents of NaOCl were taken up. It is known from the literature that vicinal glycols are cleaved to acids by ruthenium tetroxide. The reaction shown below can account for consumption of five equivalents of NaOCl.

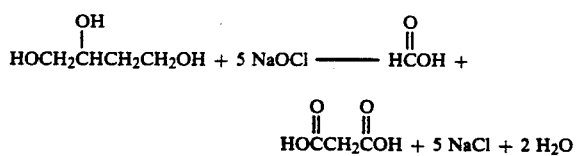

Oxidation of 1,4-butenediol did not give dehydrobutyrolactone. Nearly seven equivalents of NaOCl were taken up. The following reaction accounts for eight equivalents of NaOCl.

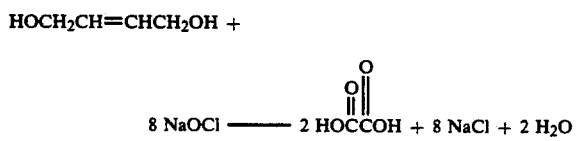

The conditions for the above reactions are those set out in the footnote to the table hereinbelow.

Suitable oxidizing agents for use in the present invention include commonly available materials, such as, NaOCl, Ca(OCl)$_2$, t-butylhydroperoxide, methyl morpholine-N-oxide, sodium periodate, and hydrogen peroxide. NaOCl and Ca(OCl)$_2$ are preferred.

Suitable ruthenium catalysts which can be used are those commercially available and include ruthenium oxide, ruthenium on carbon, ruthenium on alumina, ruthenium trichloride, H$_2$Ru(PPh$_3$)$_4$, and Cl$_2$Ru(PPH$_3$)$_4$. However, essentially any ruthenium-containing material can be used so long as the oxidant can oxidize the ruthenium to the active form.

The process of the present invention may be carried out by dissolving the diol in a suitable solvent. Solvents which may be used are those which are resistant to oxidation by the oxidizing agent. Typically, such solvents include water, ethyl acetate, acetonitrile, dimethylformamide, sulfolane, and the like. The preferred solvent is water since it is most readily available and least expensive. A catalytic amount of the ruthenium compound is then added to the solution. The catalyst may or may not dissolve in the particular solvent used. If it does dissolve, this aids in the rapidity of the reaction. Alternatively, the catalyst may be added directly to the diol without the presence of a solvent. The catalyst is dissolved in the diol and the oxidant is added directly to this mixture. The mixture is heated or cooled to the desired reaction temperature and the oxidant is added, usually in drop-wise fashion into the solution with stirring. Usually, the mixture of the diol and catalyst is colored. As the oxidant is added, the mixture or reaction solution becomes clear yellow, but then returns to the original color. As the reaction nears completion, the new color persists for longer periods eventually remains, indicating the completion of the reaction.

In this process, the amount of starting diol may vary depending on the total amount of product required. The oxidant appears to react stoichiometrically with the diol so that the total quantity of oxidant needed to complete the reaction corresponds to the stoichiometric requirements. The amount of catalyst to be added is essentially a catalytically effective amount, preferably in the range of from about 0.001 to 2.0 weight % based on the weight of the diol. The initial concentration of the diol in the solvent is from about 1.0 to 75.0 weight %, based on the total weight of solvent and diol. Preferably, the concentration of the diol is from about 5.0 to 25%.

After the completion of the reaction, the lactone obtained can be separated from the reaction mixture by conventional working up procedures, e.g., distillation, etc.

EXAMPLE 1

One gram of butane diol was dissolved in 15 cc. of water. Ten milligrams of RuCl$_3$.H$_2$O is added to the solution. At ice bath temperatures, an aqueous solution of 5.25% NaOCl was slowly dripped into the diol solution with stirring. With each additional drop of NaOCl, the solution turned from black to yellow and then quickly back to black. As the reaction neared completion, the yellow color persisted for longer periods. When the color remained yellow for 0.5 hours, the reaction was finished. The amount of NaOCl required to maintain the yellow color corresponded closely to the calculated amount needed for one gram of butane diol. Gas chromatographic analysis shows that no butane diol remained and the only material present was butyrolactone.

This reaction was carried out at a temperature range from 10° to 15° C., and the butane diol was converted quantitatively to butyrolactone in a short period of time. On a weight basis, the butane diol to RuCl$_3$.H$_2$O is 100-fold excess, while on a molar basis, the amount of butane diol to active ruthenium is 231:1. If the reactions are conducted at a higher temperature, lower levels of ruthenium can be used and still maintain a reasonable rate of reaction.

The following table illustrates a number of diols which can be converted to lactones and the yields of product obtained thereby. The selectivity of the process was followed by gas chromatographic analysis. In the table, the column entitled, "GC Selectivity" represents the percentage of the desired end-product achieved as shown on the gas chromatogram. Also illustrated in the table are the equivalents of NaOCl oxidant utilized. The gas chromatographic analysis was carried out using a DB-wax column 30 meters long with a diameter of 0.326 mm and a film thickness of 0.5 mm. The carrier gas was helium at the rate of 1 ml/min. The temperature program had an initial value of 125° C., and was increased at a rate of 4° C./ min. to a final value of 220° C. over a total of 100 minutes.

TABLE

Oxidation of Diols to Lactones*

| Exp. | Diol | Desired Product | Conversion (%) | GC Selectivity | Equivalents of NaOCl |
|---|---|---|---|---|---|
| 1 | HO—\_/—\_OH (butane diol) | γ-butyrolactone | 100 | 100 | 2.05 |
| 2** | HO—\_/—\_OH | γ-butyrolactone | 100 | 100 | 2.66 |
| 3 | HO—/\_/\_—OH (pentane diol) | δ-valerolactone | 100 | 98 | 2.10 |

TABLE-continued
Oxidation of Diols to Lactones*

| Exp. | Diol | Desired Product | Conversion (%) | GC Selectivity | Equivalents of NaOCl |
|---|---|---|---|---|---|
| 4 | HO~O~OH (with central O) | δ-valerolactone structure | 71 | 55 | 2.15 |
| 5 | norbornane-diol | norbornane-lactone | 98.6 | 98 | 2.1 |
| 6 | HO-CH2-CH(CH3)-CH2-OH (methyl-1,3-propanediol) | methyl-γ-butyrolactones (two isomers) | 97 | 41, 59 | 3.2 |
| 7 | HO-CH2-CH=CH-CH2-OH | butenolide | 100 | 0 | 6.84 |
| 8 | HO-CH2-CH(OH)-CH2-CH2-OH | hydroxy-γ-butyrolactone | 100 | 0 | 4.76 |

*All reactions except exp. 2 were run with ten mg $RuCl_3$—$H_2O$ as catalyst, 1 gram of diol in 15 cc $H_2O$. 5.25% aqueous NaOCl was used as oxidant. All reactions were run at 10–15° C.
**Catalyst was 0.2 g 5% Ru/carbon.

EXAMPLE 2

One milligram of $RuCl_3.H_2O$ was dissolved in ten grams of 1,4-butenediol. At ice bath temperature, 5.25% aqueous NaOCl was slowly added with stirring. After a total of 550 ml, all 1,4-butenediol was consumed as detected by gas chromatography. The selectivity to butyrolactone was 80%; hydroxybutyraldehyde was also observed (10% selectivity). This example demonstrates that very low levels (0.01 weight %) of catalyst can be used although selectivity drops to 80%.

What is claimed is:

1. A method for converting 1,4 and 1,5 saturated diols to lactones comprising reacting the diol in the presence of an effective amount of a chemical oxidizing agent selected from the group consisting preferably of NaOCl, $Ca(OCl)_2$, t-butylhydroperoxide, methyl morpholine-N-oxide, sodium periodate, and hydrogen peroxide and a catalytic amount of a ruthenium containing catalyst selected from the group consisting of ruthenium oxide, ruthenium on carbon, ruthenium on alumina, ruthenium trichloride, $H_2Ru(PPh_3)_4$, and $Cl_2Ru(PPh_3)_4$, wherein Ph is phenyl at a temperature from about −20° C. to ambient.

2. The method of claim 1 wherein the amount of catalyst is in the range from about 0.001 to 2 weight percent based on the amount of the starting diol.

3. The method of claim 1 wherein a solvent is present the concentration of starting diol is in the range from about 1 to 75% based on the total weight of solvent and diol.

4. The method of claim 3 wherein the concentration of starting diol is from about 5 to 25%.

5. The method of claim 1 wherein the catalyst is first dissolved in the starting diol in the absence of added solvent, and the oxidizing agent is added portion wise to the mixture until the reaction is completed.

6. The method of claim 1 wherein the starting diol is first dissolved in a solvent which is resistant to oxidation, the catalyst is admixed to the resulting solution, the temperature of the mixture is adjusted to the desired temperature and the oxidizing agent is added portion wise to the mixture until the reaction is completed.

7. The method of claim 6 wherein the solvent is selected from the group consisting of water, acetonitrile, dimethylformamide, and sulfolane.

* * * * *